US005723482A

United States Patent [19]

Degwert et al.

[11] Patent Number: 5,723,482
[45] Date of Patent: Mar. 3, 1998

[54] ACTIVE COMPOUNDS AND COSMETIC AND DERMATOLOGICAL FORMULATIONS

[75] Inventors: Joachim Degwert, Tostedt; Gerhard Sauermann, Wiemersdorf; Volkner Schreiner, Hamburg; Franz Stab, Echem, all of Germany

[73] Assignee: Beiersdorf AG, Hamburg, Germany

[21] Appl. No.: 522,268

[22] PCT Filed: Mar. 11, 1994

[86] PCT No.: PCT/EP94/00760

§ 371 Date: Sep. 12, 1995

§ 102(e) Date: Sep. 12, 1995

[87] PCT Pub. No.: WO94/21245

PCT Pub. Date: Sep. 29, 1994

[30] Foreign Application Priority Data

Mar. 13, 1993 [DE] Germany .................. 43 07 983.0

[51] Int. Cl.$^6$ .................. A61K 31/415; A61K 7/42; A61K 7/46; C09C 1/36
[52] U.S. Cl. .................. 514/399; 424/59; 424/60; 424/400; 424/401; 424/404; 512/1; 512/2; 514/400; 106/436

[58] Field of Search .................. 424/59, 60, 400, 424/401; 514/399, 484; 106/436; 512/1, 2

[56] References Cited

FOREIGN PATENT DOCUMENTS

| 0413528 | 2/1991 | European Pat. Off. . |
| 0467116 | 1/1992 | European Pat. Off. . |

*Primary Examiner*—Shelley A. Dodson
*Attorney, Agent, or Firm*—Sprung Kramer Schaefers & Briscoe

[57] ABSTRACT

Use of carnosine or derivatives or analogs thereof or of the combination of the active compounds a) carnosine or derivatives or analogs thereof and b) urocanic acid or derivatives or analogs thereof, or in each case mixtures of these compounds, if appropriate in each case in combination with an antioxidant or a plurality of antioxidants and if appropriate with a suitable carrier, for cosmetic and dermatological purposes, in particular for the prophylaxis and treatment of photosensitive skin, in particular photodermatoses, and preferably polymorphic photodermatosis.

20 Claims, No Drawings

ACTIVE COMPOUNDS AND COSMETIC AND DERMATOLOGICAL FORMULATIONS

The present invention relates to cosmetic and dermatological formulations. The invention particularly relates to active compounds and formulations which are used for prophylaxis and treatment of light-sensitive skin, in particular of photodermatoses.

The damaging effect of the ultraviolet part of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even actual burns of greater or lesser severity.

The narrower range around 308 nm is stated as the erythema activity maximum of sunlight.

Numerous compounds are known for protection against UVB radiation, these being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have available filter substances, since the rays thereof can cause reactions on light-sensitive skin. It has been proved that UVA radiation leads to damage to the elastic and collagenic fibers of connective tissue, which makes the skin age prematurely, and that it is to be regarded as a cause of numerous phototoxic and photoallergic reactions. The damaging effect of UVB radiation can be intensified by UVA radiation.

Certain derivatives of dibenzoylmethane, the photostability of which derivatives (Int. J. Cosm. Science 10, 53 (1988)) is not adequate, are therefore used for protection against rays of the UVA range.

However, UV radiation can also lead to photochemical reactions, the photochemical reaction products then intervening in skin metabolism and in the immune system and causing photodermatoses.

Such photochemical reaction products are chiefly free-radical compounds, for example hydroxy radicals. Undefined free-radical photoproducts which are formed in the skin itself can also show uncontrolled secondary reactions because of their high reactivity. However, singlet oxygen, a non-radical excited state of the oxygen molecule, may occur under UV irradiation, as can short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in biochemical processes.

It is assumed that photoinduced processes in the end lead to allergic reactions in the skin, which manifest themselves phenotypically as so-called polymorphic photodermatoses.

To prevent these reactions, antioxidants and/or agents which trap free radicals can additionally be incorporated into the cosmetic or dermatological formulations.

It has already been proposed to employ vitamin E, a substance of known antioxidative action, in light protection formulations, although here too the effect achieved falls far short of that hoped for.

It is also known to employ trans-urocanic acid (also called trans-urocaninic acid, E-urocaninic acid, E-urocanic acid, trans-(4-imidazolyl) acrylic acid or E-4-imidazolylacrylic acid) as a UV filter. However, the present invention does not relate to this use.

Examples are to be found in Japanese laid-open specifications JP-Kokai-Sho-54/027562, JP-Kokai-Sho-63/051318 and JP-Kokai-Sho-56/063965, and in the associated examined specifications.

It was therefore surprising and unforeseeable to the expert that cosmetic and dermatological formulations, in particular topical formulations, having an active content of carnosine or derivatives or analogues thereof or of the combination of the active compounds a) carnosine or derivatives or analogues thereof and b) urocanic acid or derivatives or analogues thereof or in each case mixtures of these compounds, if appropriate in each case in combination with one or more antioxidants, remedy the disadvantages of the prior art.

The invention also relates to the use of carnosine or derivatives or analogues thereof or of the combination of the active compounds a) carnosine or derivatives or analogues thereof and b) urocanic acid or derivatives or analogues thereof, or in each case mixtures of these compounds, if appropriate in each case in combination with an antioxidant or a plurality of antioxidants, for the prophylaxis and treatment of light-sensitive skin, in particular photodermatoses, and preferably polymorphic photodermatosis.

The invention particularly relates to the use of cosmetic and dermatological formulations, in particular topical formulations, having an active content of carnosine or derivatives or analogues thereof or of the combination of the active compounds a) carnosine or derivatives or analogues thereof and b) urocanic acid or derivatives or analogues thereof, or in each case mixtures of these compounds, if appropriate in each case in combination with one or more antioxidants, for the prophylaxis and treatment of light-sensitive skin, in particular photodermatoses, and preferably polymorphic photodermatosis.

Instead of carnosine, derivatives and analogues of carnosine (for example anserine), especially those from which carnosine is formed during use, can also be employed.

Instead of urocanic acid, derivatives and analogues of urocanic acid, especially those from which urocanic acid is formed during use, can also be employed.

D,L-carnosine, L-carnosine, D-carnosine, D,L-anserine, L-anserine, D-anserine or salts or acid addition salts thereof, preferably water-soluble salts, for example sodium, potassium and ammonium salts, and esters thereof with alcohols, for example monoalcohols or sugars, can preferably be used as the carnosine or derivatives or analogues thereof.

Preferred monoalcohols are saturated or unsaturated, preferably mono-, di- or tri-unsaturated, monoalcohols having in particular 1 to 18, particularly preferably 14 to 18, carbon atoms.

Preferred esters are carnosine hexadecyl ester, carnosine octadecyl ester, carnosine oleyl ester, carnosine Z,Z-9,12-octadecadienyl ester, carnosine Z,Z,Z-9,12,15-octadecatrienyl ester, carnosine Z,Z,Z-6,9,12-octadecatrienyl ester, cholesterylcarnosine and the methyl, ethyl, butyl, propyl, amyl, sorbityl, galactosyl, mannosyl, glucosyl, glycosyl and glyceryl ester of carnosine, and esters with thiol compounds, in particular the thiol compounds which correspond to the above alcohols.

Carnosine or anserine, in particular L-carnosine or L-anserine, are preferred.

Cis-urocanic acid, trans-urocanic acid or mixtures thereof, L-histidine, D- and D,L-histidine and derivatives or analogues thereof, in particular physiological derivatives and analogues, such as imidazoleglycerol, imidazoleglycerol phosphate, imidazoleacetol phosphate, 5-aminoimidazole-4-carboxamide ribonucleotide, 4-imidazolone-5-propionic acid, imidazole acetate, L-histidinol, L-histidinol phosphate, L-histidinol acetate, L-histidinol palmitate or oleate or L-histidinal, can preferably be used as the urocanic acid or derivatives and analogs thereof.

Imidazole, 2- or 3-pyrroleacrylic acid, 2- or 3-furylacrylic acid, 2-thiopheneacrylic acid and 3-thiopheneacrylic acid, wherein the acrylic acid is substituted in the beta-position, are furthermore preferred. Compounds which are hydrogenated in the heterocyclic ring, in particular in the imidazole ring, in particular dihydrourocanic acid, are also preferred.

Imidazole rings can also be substituted in the 2-position, and the 2-methyl, 2-ethyl, 2-propyl and 2-acetyl derivatives, in particular of urocanic acid, are preferred.

The salts and addition salts and esters of urocanic acid and derivatives and analogues thereof, in particular the salts and esters stated above for carnosine, are also preferred.

Histidine, imidazoleglycerol, imidazole glycerol phosphate, imidazolone-5-propionic acid, imidazole acetate, L-histidinol, L-histidinol phosphate, L-histidinol acetate, L-histidinol palmitate and oleate, L-histidine, cis- or trans-urocanic acid and mixtures thereof are particularly preferred.

One active compound can be used according to the invention, or it is also possible to use a plurality of active compounds from the group of active compounds as a mixture.

Combinations of the active compounds of carnosine, in particular L-carnosine and cis-urocanic acid or trans-urocanic acid or mixtures of cis- and trans-urocanic acid or histidine or mixtures of these compounds with two or more active compounds are particularly preferred.

Other names for polymorphic photodermatosis are PPD, PPE, Mallorca acne and a large number of other names, such as are mentioned in the literature (for example A. Voelckel et al., Zentralblatt Haut- and Geschlechtskrankheiten (1989), 156, page 2).

The invention also relates to the mixtures of active compounds and formulations containing them.

The invention also relates to the new combinations of active compounds, in particular cosmetic and dermatological combinations.

The combinations of L-carnosine with cis- and/or trans-urocanic acid are particularly preferred.

Formulations according to the invention which additionally contain a UV protection agent or light protection agent are particularly preferred.

The subject matter according to the invention stated in the claims is also part of the present invention and of the description.

It was not foreseeable that the active compounds according to the invention or the cosmetic or dermatological formulations according to the invention with these act against PPE.

It was also not foreseeable that the active compounds according to the invention or the cosmetic or dermatological formulations according to the invention would have a sufficiently high stability for use lead to products tolerated by the skin not intervene in the endogenous microorganism flora of the skin increase the skin moisture and compensate washing out of the endogenous urocanic acid of the skin.

It was furthermore surprising that the active compounds according to the invention would be active in relevant photochemically induced immunological processes in and on the human skin, and can be used in particular for prophylaxis and treatment of light-sensitive skin, in particular photodermatoses, and preferably polymorphic photodermatosis.

It is indeed known from DE-A 41 21 030 to add cis-urocanic acid to dermatological formulations which result in various actions, including antipsoriatic, antiallergic and the like. However, at no point does this document even suggest the advantageous properties of cis-urocanic acid. A combination of L-carnosine and cis- and/or trans-urocanic acid and/or histidine, in particular, surprisingly leads to success for the prophylaxis and treatment of PPE.

The active compounds, combinations and formulations obtained with these according to the invention have a prophylactic action in that they protect light-sensitive skin and reduce or alleviate the development of PPE. For this purpose, they are used before exposure to solar radiation.

In the case of manifest PPE, an improvement in states of the skin and a faster subsidence of the PPE occurs with treatment with the active compound and formulations according to the invention.

The cosmetic and/or dermatological formulations according to the invention can have the customary composition and can be used for treatment, care and cleansing of the skin and/or hair and as a make-up product in decorative cosmetics. They preferably comprise in each case 0.01% by weight to 20% by weight, but in particular 0.1% by weight to 6% by weight, based on the total weight of the composition, of the active compounds according to the invention or mixtures thereof.

The weight contents of active compounds of groups a and b in the combinations can be varied within a wide range of ratios. The weight ratio of the active compounds a/b is preferably 1000:1 to 1:1000, in particular 100:1 to 1:100, particularly preferably 10:1 to 1:10.

Combinations with a high or predominant weight content of carnosine or derivatives or analogs thereof are particularly preferred. The weight ratio of the active compounds a/b can thus preferably be 100:1, in particular 10:1.

Nevertheless, reference is made to the corresponding legislation of individual countries which specifies maximum values for active compound concentrations in the individual case. In Germany, at the current point in time, the maximum concentration of urocanic acid (cis and trans isomer taken together) is limited to 2.0% by weight, based on the total weight of the composition.

For use, the cosmetic and dermatological formulations according to the invention are applied to the skin and/or the hair in an adequate amount in the manner customary for cosmetics.

The outstanding action of the active compounds and combinations according to the invention on light-sensitive skin, photodermatoses and PPD can be demonstrated by in vitro experiments.

Studies on the human epidermis which had first been treated in vivo with a combination which is active according to the invention, for example of L-carnosine and cis-urocanic acid, and had then been irradiated in vitro with UV light thus showed that the immunomodulating photochemical effect of UV light surprisingly can thereby be eliminated or at least lessened. Similar results were obtained, surprisingly, when primary cultures of human epidermis cells were irradiated in vitro and cocultured with combinations according to the invention of carnosine and urocanic acid.

These studies were carried out by means of the so-called mixed epidermis cell lymphocyte reaction assay (MECLR) in accordance with the method of U. D. Cooper et al. (published 1985 in J. Immunol. 134, pages 129–137). Human epidermis was obtained by means of the suction blister method applying a reduced pressure of 200 mbar (U. Kiistala et al., 1964, Lancet 1, page 1444). The cell suspension obtained therefrom by means of trypsin treatment was then irradiated with a UV dose of 7.5 mJ/cm$^2$ and cocultured in a ratio of 1:1 with peripheral blood leucocytes (PBL) from an allogenic donor in microtiter plates for 6 days. The combinations according to the invention of active substances were added to the cell culture batches in different concentrations at the start of the 6-day cell culture. Combinations, for example, of urocanic acid and carnosine in a molar ratio of 10:1 to 1:100 for the ratio of urocanic acid/carnosine proved to be particularly active here in reducing a UV-induced immunomodulation.

Those cosmetic and dermatological formulations which are in the form of a sunscreen agent are particularly preferred. These preferably additionally comprise at least one UVA filter and/or at least one further UVB filter and/or at least one inorganic pigment.

Cosmetic and dermatological formulations according to the invention for protection of the skin against UV rays can be in various forms, such as are usually employed, for example, for this type of formulation. They can thus be, for example, a solution, an emulsion of the water-in-oil type (W/O) or of the oil-in-water type (O/W), or a multiple emulsion, for example of the water-in-oil-in-water (W/O/W) type, a gel, a solid stick or else an aerosol.

The cosmetic and dermatological formulations according to the invention can comprise cosmetic auxiliaries such as are usually used in such formulations, for example preservatives, bactericides, perfumes, substances for preventing foaming, dyes, pigments which have a coloring action, thickeners, surface-active substances, emulsifiers, softening humidifying and/or humectant substances, fats, oils, waxes or other customary constituents of a cosmetic or dermatological formulation, such as alcohols, polyols, polymers, foam stabilizers, electrolytes, organic solvents or silicone derivatives.

If the cosmetic or dermatological formulation is a solution or lotion, solvents which can be used are:

water or aqueous solutions oils, such as triglycerides of capric or of caprylic acid, but preferably castor oil;

fats, waxes and other naturally occurring and syn- thetic fat substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. Water can be a further constituent of alcoholic solvents.

Emulsions according to the invention, for example in the form of a sunscreen cream or a sunscreen milk, are preferred and comprise, for example, the fats, oils, waxes and other fat substances mentioned, as well as water and an emulsifier such as is usually used for such a type of formulation.

Gels according to the invention usually comprise alcohols of low C number, for example ethanol, isopropanol, 1,2-propanediol, glycerol and water, or abovementioned oil in the presence of a thickener, which is preferably silicon dioxide or an aluminium silicate in oily-alcoholic gels and is preferably a polyacrylate in aqueous-alcoholic or alcoholic gels.

Solid sticks according to the invention comprise, for example, naturally occurring or synthetic waxes, fatty alcohols or fatty acid esters. Lip care sticks are preferred.

Suitable propellants for cosmetic deodorants according to the invention which can be sprayed from aerosol containers are the customary known readily volatile, liquefied propellants, for example hydrocarbons (propane, butane, isobutane), which can be employed by themselves or as a mixture with one another. Compressed air can also advantageously be used.

The expert of course knows that there are propellant gases which are non-toxic per se and which would be suitable in principle for the present invention, but which should nevertheless be omitted because of an unacceptable action on the environment or other concomitant circumstances, these gases being especially fluorohydrocarbons and chlorofluorohydrocarbons (CFCs).

Preferred antioxidants are thiols, for example cysteine and cysteine derivatives, glutathione, cystine, N-acetylcysteine, liponic acid, folic acid, ubiquinone, phytic acid, alpha-hydroxy acids, for example citric acid and lactic acid, zinc sulphate, zinc oxide, vitamin C, vitamin E and carotene.

The cosmetic or dermatological formulations according to the invention comprise antioxidants, for example, in amounts of 0.01% by weight to 10% by weight, preferably in amounts of 0.5% by weight to 6% by weight, but in particular 2% by weight to 4% by weight, based on the total weight of the formulations.

They can furthermore preferably comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also be used as sunscreen agents.

The UVB filters can be oil-soluble or water-soluble. Oil-soluble substances which may be mentioned are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate;

2,4,6-trianilino-(p-carbo-2'-ethyl-1'-hexyloxy)-1,3,5-triazine.

Water-soluble substances which may be mentioned are, for example:

- salts of 2-phenylbenzimidazole-5-sulphonic acid, such as its sodium, potassium or its triethanol-ammonium salt, and the sulphonic acid itself;

- sulphonic acid derivatives of benzophenones, preferably 2-hydroxy-4-methoxybenzophenone-5-sulphonic acid and its salts;

- sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)benzenesulphonic acid and their salts.

The list of UVB filters mentioned is of course not intended to be limiting.

The invention also relates to formulations according to the invention with combinations of a UVA filter with a UVB filter and to cosmetic or dermatological formulations according to the invention which also comprise a UVB filter.

It may also be advantageous to combine the active compounds according to the invention with UVA filters which have usually been contained to date in cosmetic formulations. These substances are preferably derivatives of dibenzoylmethane, in particular 1-(4'-tert-butyl-phenyl)-3-(4'-methoxyphenyl)propane-1,3-dione and 1-phenyl-3-(4'-isopropylphenyl)propane-1,3-dione. The invention also relates to these combinations and to formulations which comprise these combinations. The amounts used for the UVA combination can be employed.

Cosmetic and dermatological formulations according to the invention can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide. The invention also relates to these combinations of UVA filter and pigment and to formulations which comprise these combinations. The amounts mentioned for the above combinations can be used.

Unless stated otherwise, all the amounts data, contents and percentage contents are based on the weight and the total amount or on the total weight of the formulations.

The invention also relates to a process for the preparation of the cosmetic compositions according to the invention, which is characterized in that the active compounds according to the invention are incorporated into cosmetic and dermatological formulations in a manner known per se.

The following examples are intended to illustrate the present invention without limiting it.

UCA means urocanic acid. The formulations of the examples show an outstanding action in the prophylaxis and treatment of sensitive skin, photodermatoses and PPD.

The formulations are prepared in a manner known per se, in particular by mixing the constituents, if appropriate at elevated temperature. The oily and aqueous phases are prepared separately and mixed or emulsified, if appropriate at elevated temperature.

EXAMPLE 1

Aqueous Formulation (Face Lotion)

| PEG 40-hydrogenated castor oil | % by weight |
|---|---|
|  | 0.811 |
| Dipropylene glycol | 2.534 |
| PEG 8 | 1.521 |
| Na₃EDTA | 0.253 |
| Polymer JR 125 | 0.025 |
| trans-UCA | 0.750 |
| L-carnosine | 7.000 |
| Water CDS | to 100.000 |

(CDS = completely desalinated)

EXAMPLE 2

Aqueous Composition

|  | % by weight |
|---|---|
| Poly-fatty acid ester (Cetiol HE) | 16.000 |
| PPG 3 myristyl ether (Witconol APM) | 1.000 |
| Propylene glycol | 3.000 |
| Glycerol | 40.000 |
| cis-UCA | 0.500 |
| L-Carnosine | 5.000 |
| Water CDS | to 100.000 |

EXAMPLE 3

Hydrogel (Polyacrylate Gel)

|  | % by weight |
|---|---|
| Acrylic acid polymer (Carbopol 934) | 1.000 |
| tris(hydroxymethylamino)methane (Tris) | 1.000 |
| Glycerol | 2.000 |
| Propylene glycol | 2.000 |
| cis-UCA | 0.050 |
| L-Carnosine | 2.000 |
| Water CDS | to 100.000 |

(instead of L-carnosine, the same amount by weight of D,L-carnosine palmityl ester can also be used).

EXAMPLE 4

Formulation of High Water Content (Very Soft)

|  | % by weight |
|---|---|
| Ceteareth (Cremophor A 25) | 0.100 |
| Cetearyl alcohol (Lanette O) | 0.400 |
| Vaseline, DAB 9 | 12.500 |
| Mineral oil, DAB 9 | 11.000 |
| Ceteareth-6-stearyl alcohol (Cremophore A6) | 6.000 |
| cis-UCA | 0.020 |
| L-carnosine | 1.000 |
| Water CDS | to 100.000 |

(instead of cis-UCA, the same amounts by weight of trans- or cis-dihydrourocanic acid can also be used)

EXAMPLE 5

Formulation of High Water Content (Soft)

| | % by weight |
|---|---|
| Ceteareth-25 (Cremophor A25) | 1.500 |
| Cetearyl alcohol (Lanette O) | 8.500 |
| cis-UCA | 0.250 |
| D,L-Carnosine | 4.000 |
| Water CDS | to 100.000 |

(instead of cis-UCA, the same amount by weight of trans-UCA galactosyl ester can also be used)

EXAMPLE 6

Formulation of High Water Content (Soft)

| | % by weight |
|---|---|
| Ceteareth-25 (Cremophor A25) | 2.000 |
| Cetearyl alcohol (Lanette O) | 8.000 |
| Vaseline, DAB 9 | 10.000 |
| Mineral oil, DAB 9 | 10,000 |
| trans-UCA | 0.100 |
| L-Carnosine | 1.000 |
| Water CDS | to 100.000 |

(instead of L-carnosine, the same amount by weight of L-anserine can also be used)

EXAMPLE 7

Formulation of High Water Content (Medium-Firm)

| | % by weight |
|---|---|
| Ceteareth-25 | 3.000 |
| Cetearyl alcohol (Lanette O) | 17.000 |
| cis-UCA | 0.175 |
| L-Carnosine | 10.000 |
| Water CDS | to 100.000 |

EXAMPLE 8

Thinly Liquid Lotion

| | % by weight |
|---|---|
| Ceteareth-25 (Cremophor A25) | 1.000 |
| Ceteareth-6-stearyl alcohol (Cremophor AG) | 1.000 |
| Glycerol mono/distearate (Tegin normal) | 2.000 |
| Cetyl alcohol | 1.000 |
| Isopropyl myristate | 1.450 |
| Glycerol | 1.000 |
| Polyvinylpyrrolidone | 0.500 |
| cis-UCA | 0.125 |
| L-Carnosine | 5.000 |
| Water CDS | to 100.000 |

EXAMPLE 9

Viscous Lotion

| | % by weight |
|---|---|
| Ceteareth 25 (Cremophor A25) | 2.000 |
| Cetearyl alcohol (Lanette O) | 3.000 |
| Mineral oil, DAB 9 | 5.000 |
| Propylene glycol | 3.000 |
| Polyvinylpyrrolidone | 0.500 |
| cis-UCA | 0.300 |
| L-Carnosine | 2.000 |
| Water CDS | to 100.000 |

(instead of L-carnosine, the same amount by weight of L-carnosine Z,Z-9,12-octadecadienyl ester can also be used)

EXAMPLE 10

W/O Cream

| | % by weight |
|---|---|
| Glycerol sorbitan fatty acid ester (Arlacel 481) | 6.000 |
| Microcrystalline wax (Lunacera M) | 1.000 |
| Neutral oil | 3.000 |
| Paraffin oil | 19.000 |
| Magnesium stearate | 1.000 |
| Propylene glycol | 3.700 |
| Magnesium sulphate ($MgSO_4 \cdot 7H_2O$) | 0.700 |
| trans-UCA | 1.000 |
| L-Carnosine | 0.800 |
| Water CDS | to 100.000 |

(instead of L-carnosine, the same amount by weight of D,L-carnosine ethyl ester can also be used)

EXAMPLE 11

W/O Emulsion

| | % by weight |
|---|---|
| Polyoxyethylene glycerol sorbitan fatty acid ester (Arlacel 988) | 3.600 |
| Polyoxyethylene fatty acid ester (Arlacel 989) | 1.400 |
| Cetearyl alcohol (Lanette O) | 2.000 |
| Mineral oil, DAB 9 | 25.000 |
| Paraben mixture | as desired |
| Magnesium sulphate ($MgSO_4 \cdot 7H_2O$) | 0.700 |
| trans-UCA | 1.250 |
| L-Carnosine | 0.600 |
| Water CDS | to 100.000 |

EXAMPLE 12

W/O Lotion

| | % By weight |
|---|---|
| Glycerol sorbitan fatty acid ester (Arlacel 481) | 1.300 |
| Polyoxyethylene fatty acid ester (Arlacel 989) | 3.700 |
| Neutral oil (Miglyol) | 6.000 |
| Paraffin oil, DAB 9 | 14.000 |
| Propylene glycol | 3.800 |
| Magnesium sulphate ($MgSO_4 \cdot 7H_2O$) | 0.700 |

-continued

| | % By weight |
|---|---|
| cis-UCS | 0.060 |
| L-Carnosine | 5.000 |
| Water CDS | to 100.000 |

(instead of cis-UCA, the same amount of cis-2-ethylurocanic acid can also be used)

EXAMPLE 13

O/W Emulsion

| | % by weight |
|---|---|
| PEG 100 stearate (Arlacel 165) | 5.000 |
| Cetearyl alcohol (Lanette O) | 3.000 |
| Mineral oil, DAB 9 | 25.000 |
| Paraben mixture | as desired |
| cis-UCA | 0.325 |
| L-Carnosine | 0.500 |
| Water CDS | to 100.000 |

(instead of cis-UCA, the same amount by weight of cis-UCA glucosyl ester can also be used)

EXAMPLE 14

O/W Emulsion

| | % by weight |
|---|---|
| Polysorbate 60 (Tween 60) | 3.000 |
| Sorbitan stearate (Arlacel 60) | 2.000 |
| Cetearyl alcohol (Lanette O) | 3.000 |
| Mineral oil, DAB 9 | 25.000 |
| Paraben mixture | as required |
| cis-UCA | 0.035 |
| L-Carnosine | 6.000 |
| Water CDS | to 100.000 |

(instead of cis-UCA, the same amount by weight of cis-UCA sorbityl ester can also be used)

EXAMPLE 15

Cationic Emulsion

| | % by weight |
|---|---|
| Distearyldimethylammonium chloride (Genamin DS AC) | 5.000 |
| Vaseline, DAB 9 | 5.000 |
| Isopropyl palmitate | 2.000 |
| Cetyl alcohol | 1.000 |
| Silicone oil | 0.100 |
| Propylparaben | 0.100 |
| Methylparaben | 0.100 |
| Glycerol | 4.000 |
| cis/trans-UCA | 0.090 |
| L-Carnosine | 1.000 |
| Water CDS | to 100.000 |

EXAMPLE 16

Ionic Emulsion

| | % by weight |
|---|---|
| Sodium cetearyl sulphate (Emulgade F) | 6.000 |
| Mineral oil, DAB 9 | 25.000 |
| Paraben mixture | as required |
| L-Histidine | 0.450 |
| L-Carnosine | 0.250 |
| Water CDS | to 100.000 |

(instead of L-carnosine, the same amount by weight of D-carnosine can also be used)

EXAMPLE 17

Ionic O/W Emulsion

| | % by weight |
|---|---|
| Stearic acid | 5.000 |
| Cetearyl alcohol (Lanette O) | 3.000 |
| Mineral oil, DAB 9 | 25.000 |
| Paraben mixture | as required |
| Triethanolamine | 1.000 |
| L-Carnosine | 8.000 |
| Water CDS | to 100.000 |

EXAMPLE 18

Sun Oil

| | |
|---|---|
| L-Carnosine | 7.0 g |
| cis-UCA | 13.0 g |
| trans-UCA | 10.0 g |
| 3-(4'-methylbenzylidene) camphor ("Eusolex 6300", Merck) | 60.0 g |
| Myristyl alcohol, polyoxypropylated with 3 mol of propylene oxide ("Witconol APM", Witco) | 608.0 g |
| $C_{12}$-$C_{15}$-alcohol benzoate ("Finsolv TN", Witco) | 152.0 g |
| Glycerol monococoate, polyoxyethylated with 7 mol of ethylene oxide ("Cetiol HE", Henkel KGaA) | 100.00 g |
| Ethanol | 65.0 g |
| 2-Octadodecanol | 20.0 g |
| Perfume, correctants, additives, antioxidants, stabilizers | as desired |

The constituents of the sun oil are mixed with one another and, if appropriate, heated to 40° to 50° C. at the same time for homogenization.

EXAMPLE 19

Sun Gel

| | |
|---|---|
| L-Carnosine | 10.0 g |
| trans-UCA | 8.0 g |
| 2,4,6-trainilino-(p-carbo-2'-ethyl-hexyl-1'-oxy)-1,3,5-triazine ("Uvinul" T-150, BASF) | 25.0 g |
| Isopropyl myristate | 189.0 g |
| $C_{12}$-$C_{15}$-alcohol benzoate ("Finsolv TN", Witco | 76.0 g |
| Myristyl alcohol, polyoxypropylated | 304.0 g |

-continued

| | |
|---|---|
| with 3 mol of propylene oxide ("Witconol APM", Witco) | |
| Caprylic/capric acid triglyercide ("Miglyol-Neutralöl", Dynamit-Nobel) | 195.0 g |
| "Bentone-38", Kronos-Titan | 150.0 g |
| Propylene carbonate | 20.0 g |
| Ethanol | 23.0 g |
| Perfume, correctants, additives, antioxidants, stabilizers | as desired |

A sun gel is prepared in the customary manner with the constituents mentioned.

EXAMPLE 20

Hydrogel

| | |
|---|---|
| L-Carnosine | 10.0 g |
| cis-UCA | 5.0 g |
| 2-Phenylbenzimidazole-5-sulphonic acid ("Eusolex 232", Merck) | 27.0 g |
| Allantoin | 2.0 g |
| Sorbitol, liquid ("Karion PI", Merck) | 22.0 g |
| "Carbopol 934", B.F. Goodrich | 15.0 g |
| Tris(hydroxymethyl)aminomethane | 27.0 g |
| Propylene glycol | 10.0 g |
| Ethanol | 300.0 g |
| Water | 582.0 g |
| Perfume, correctants, additives, antioxidants, stabilizers | as desired |

A hydrogel is prepared in the customary manner with the constituents mentioned.

EXAMPLE 21

Oil-in-water Emulsion (Suncream)

| | |
|---|---|
| L-Carnosine | 4.0 g |
| cis-UCA | 16.0 g |
| 2-Phenylbenzimidazole-5-sulphonic acid ("Eusolex 232", Merck) | 32.0 g |
| Stearyl alcohol oxyethylated with 2 mol of ethylene oxide ("Brij 72", ICI) | 30.0 g |
| Stearyl alcohol oxyethylated with 21 mol of ethylene oxide ("Brij 721", ICI) | 20.0 g |
| Cetylstearyl alcohol | 25.0 g |
| Myristyl alcohol, polyoxypropylated with 3 mol of propylene oxide ("Witconol APM", Witco) | 64.0 g |
| $C_{12}$-$C_{15}$-alcohol benzoate ("Finsolv TN", Witco) | 16.0 g |
| Propylene glycol | 35.0 g |
| Tris(hydroxymethyl)aminomethane | 14.0 g |
| Water | 744.0 g |
| Perfume, correctants, additives, antioxidants, stabilizers | as desired |

The fat substances are heated to 80° to 85° C. The water-soluble constituents, including the cis-urocanic acid and L-carnosine, are dissolved in water at the same temperature, the two phases are mixed with one another, while stirring vigorously, and the mixture is allowed to cool, while stirring more moderately.

EXAMPLE 22

Oil-in-water Emulsion (Suncream)

| | |
|---|---|
| L-Carnosine | 13.0 g |
| cis/trans-UCA (1:1) | 20.0 g |
| 2,4,6-Trianilino-(p-carbo-2'-ethyl-hexyl-1'-oxy)-1,3,5-triazine ("Uvinul T-150", BASF) | 18.0 g |
| $C_{12}$-$C_{15}$-Alcohol benzoate ("Finsolv TN", Witco) | 47.0 g |
| Cetylstearyl alcohol | 30.0 g |
| Mixture of stearic acid mono- and diesters of glycerol and stearic acid esters of polyethylene oxide ("Arlacel 165", ICI) | 50.0 g |
| Myristyl alcohol, polyoxypropylated with 3 mol of propylene oxide ("Witconol APM", Witco) | 185.0 g |
| Water | 637.0 g |
| Perfume, correctants, additives, antioxidants, stabilizers | as desired |

The Emulsion is prepared in accordance with the above example.

EXAMPLE 23

Water-in-oil Emulsion (Sunscreen Milk)

| | |
|---|---|
| L-Carnosine | 10.0 g |
| trans-UCA | 10.0 g |
| 1-(4'-tert-Butylphenyl)-3-(4'-methoxy-phenyl)-propane-1,3-dione ("Parsol 1789", Givaudan) | 15.0 g |
| 2-Ethylhexyl 4-methoxycinnamate ("Parsol MCX", Givaudan) | 35.0 g |
| Esters of saturated fatty acids with polyethylene oxide ("Arlacel 989", ICI) | 37.0 g |
| Esters of unsaturated fatty acids with glycerol and sorbitan ("Arlacel 481", ICI) | 13.0 g |
| Myristyl alcohol, polyoxypropylated with 3 mol of propylene oxide ("Witconol APM", Witco) | 160.0 g |
| $C_{12}$-$C_{15}$-Alcohol benzoate ("Finsolv TN", Witco) | 40.0 g |
| Magnesium sulphate heptahydrate | 7.0 g |
| Water | 673.0 g |
| Perfume, correctants, additives, antioxidants, stabilizers | as desired |

The Emulsion is prepared in a manner corresponding to that described under Example 21.

EXAMPLE 24

Water-in-oil Emulsion (Sunscreen Milk)

| | |
|---|---|
| L-Carnosine | 7.0 g |
| cis-UCA | 7.0 g |
| 2-Ethylhexyl 4-methoxycinnamate ("Parsol MCX", Givaudan) | 15.0 g |
| 3-(4'-Methylbenzylidene)camphor ("Eusolex 6300", Merck) | 3.0 g |
| Esters of unsaturated fatty acids with glycerol and sorbitan ("Arlacel 481", ICI) | 60.0 g |
| Microwax ("Lunacera 11", Fuller) | 10.0 g |
| Caprylic/capric acid triglyceride ("Miglyol-Neutralöl", Dynamit-Nobel) | 20.0 g |

-continued

| Myristyl alcohol, polyoxypropylated with 3 mol of propylene oxide ("Witconol APM", Witco) | 145.0 g |
|---|---|
| C$_{12}$–C$_{15}$-Alcohol benzoate ("Finsolv TN", Witco) | 37.0 g |
| Magnesium stearate | 10.0 g |
| Propylene glycol | 37.0 g |
| Magnesium sulphate heptahydrate | 7.0 g |
| Water | 641.0 g |
| Perfume, correctants, additives antioxidants, stabilizers | as desired |

The Emulsion is prepared in a manner corresponding to that described under Example 21.

EXAMPLE 25

Water-in-oil Emulsion (Sunscreen Milk)

| UCA + L-carnosine (1:1) | 33.0 g |
|---|---|
| 2-Ethylhexyl 4-methoxycinnamate ("Parsol MCX", Givaudan) | 15.0 g |
| 3-(4'-Methylbenzylidene)camphor ("Eusolex 6300", Merck) | 3.0 g |
| Esters of unsaturated fatty acids with glycerol and sorbitan ("Arlacel 481", ICI) | 60.0 g |
| Microwax ("Lunacera 11", Fuller) | 10.0 g |
| Caprylic/capric acid triglyceride ("Miglyol-Neutralöl", Dynamit-Nobel) | 20.0 g |
| Myristyl alcohol, polyoxypropylated with 3 mol of propylene oxide ("Witconol APM", Witco) | 119.0 g |
| C$_{12}$–C$_{15}$-Alcohol benzoate ("Finsolv TN", Witco) | 30.0 g |
| Magnesium stearate | 10.0 g |
| Propylene glycol | 37.0 g |
| Magnesium sulphate heptahydrate | 7.0 g |
| Water | 656.0 g |
| Perfume, correctants, additives, antioxidants, stabilizers | as desired |

The emulsion is prepared in the same manner as described under Example 21.

We claim:

1. A cosmetic or dermatological formulation which comprises an effective amount of
   a) carnosine or a derivative or analogue thereof;
   b) urocanic acid or a derivative or an analogue thereof;
   c) optionally an antioxidant; and
   d) an auxiliary.

2. The formulation according to claim 1, wherein the carnosine or a derivative or analogue thereof is selected from the group consisting of carnosine, L-carnosine, anserine or L-anserine and the urocanic acid or derivative or analogue thereof is selected from the group consisting of histidine, imidazole-glycerol, imidazoleglycerol phosphate, imidazolone-5-propionic acid, imidazole acetate, L-histidinol, L-histidinol phosphate, L-histidinol acetate, L-histidinol palmitate or oleate, L-histidine, cis- or trans-urocanic acid.

3. The formulation according to claim 1, which additionally contains a light protection agent or a UV protection agent.

4. The formulation according to claim 3, wherein the UV protection agent is a UVB filter selected from the group consisting of 3-benzylidenecamphor derivatives, 4-aminobenzoic acid derivatives, esters of cinnamic acid, esters of salicylic acid, derivatives of benzophenone, esters of benzamalonic acid, 2,4,6-trianilino-(p-carbo-2'-ethyl-1'-hexyloxy)-1,3,5-triazine, salts of 2-phenylbenzimidazole-5-sulphonic acid, sulphonic acid derivatives of benzophenones and sulphonic acid derivatives of 3-benzylidenecamphor.

5. The formulation according to claim 3, wherein the UV protection agent is a UVA filter selected from the group consisting of a derivative of dibenzoylmethane, 1-(4'-tert-butylphenyl)-3-(4'-methoxyphenyl)propane-1,3-dione or 1-phenyl-3-(4'-isopropylphenyl)propane-1,3-dione.

6. The formulation according to claim 1, which additionally contains an inorganic pigment.

7. The formulation according to claim 6, wherein the inorganic pigment is based upon titanium dioxide.

8. The formulation according to claim 1, wherein the auxiliary is a preservative, a bactericide, a perfume, an agent for preventing foam, a dye, a pigment, a thickener, a surface-active agent, an emulsifier, a softening agent, a humidifying agent, a humectant, a fat, an oil, a wax, an alcohol, a polyol, a polymer, a foam stabilizer, an electrolyte, an organic solvent or a silicone derivative.

9. The formulation according to claim 1, which is in the form of a solution or lotion, an emulsion or an oily-alcoholic gel, an aqueous-alcoholic gel, or an alcoholic gel or is in the form of a stick or an aerosol.

10. A method for the prophylaxis or for the treatment of the condition of light-sensitive skin or hair which comprises topically applying to the skin a cosmetically or dermatologically effective amount of the formulation according to claim 1.

11. The method according to claim 10, wherein the condition is photodermatosis.

12. The method according to claim 11, wherein the photodermatosis is polymorphic dermatosis.

13. The method according to claim 10, wherein the carnosine or a derivative or analogue thereof in the formulations is selected from the group consisting of carnosine, L-carnosine, anserine or L-anserine and the urocanic acid or derivative or analogue thereof is selected from the group consisting of histidine, imidazole-glycerol, imidazoleglycerol phosphate, imidazolone-5-propionic acid, imidazole acetate, L-histidinol, L-histidinol phosphate, L-histidinol acetate, L-histidinol palmitate or oleate, L-histidine, cis- or trans-urocanic acid.

14. The method according to claim 10, wherein the formulation additionally contains a light protecting agent or a UV protecting agent.

15. The method according to claim 14, wherein the UV protecting agent is a UVB filter selected from the group consisting of 3-benzylidenecamphor derivatives, 4-aminobenzoic acid derivatives, esters of cinnamic acid, esters of salicylic acid, derivatives of benzophenone, esters of benzamalonic acid, 2,4,6-trianilino-(p-carbo-2'-ethyl-1'-hexyloxy)-1,3,5-triazine, salts of 2-phenylbenzimidazole-5-sulphonic acid, sulphonic acid derivatives of benzophenones and sulphonic acid derivatives of 3-benzylidenecamphor.

16. The method according to claim 14, wherein the UV protecting agent is a UVA filter selected from the group consisting of a derivative of dibenzoylmethane, 1-(4'-tert-butylphenyl)-3-(4'-methoxyphenyl)propane-1,3-dione or 1-phenyl-3-(4'-isopropylphenyl)propane-1,3-dione.

17. The method according to claim 14, wherein the formulation additionally contains an inorganic pigment.

18. The method according to claim 14, wherein the inorganic pigment is based upon titanium dioxide.

19. The method according to claim 10, wherein the formulation additionally contains an auxiliary and the auxiliary is a preservative, a bactericide, a perfume, an agent for preventing foam, a dye, a pigment, a thickener, a surface-active agent, an emulsifier, a softening agent, a humidifying agent, a humectant, a fat, an oil, a wax, an alcohol, a polyol, a polymer, a foam stabilizer, an electrolyte, an organic solvent or a silicone derivative.

20. The method according to claim 10, wherein the formulation is in the form of a solution or lotion, an emulsion or an oily-alcoholic gel, an aqueous-alcoholic gel, or an alcoholic gel or is in the form of a stick or an aerosol.

* * * * *